(12) United States Patent
Vogel

(10) Patent No.: US 8,643,228 B2
(45) Date of Patent: Feb. 4, 2014

(54) LINEAR MOTOR WITH PERMANENT-MAGNETIC SELF-HOLDING

(75) Inventor: Walter Vogel, Trossingen (DE)

(73) Assignee: Karl Storz GmbH & Co. KG (DE)

( * ) Notice: Subject to any disclaimer, the term of this patent is extended or adjusted under 35 U.S.C. 154(b) by 181 days.

(21) Appl. No.: 13/035,706

(22) Filed: Feb. 25, 2011

(65) Prior Publication Data

US 2011/0210690 A1  Sep. 1, 2011

(30) Foreign Application Priority Data

Feb. 26, 2010  (DE) .......................... 10 2010 000 582

(51) Int. Cl.
*H02K 41/00* (2006.01)

(52) U.S. Cl.
USPC ..................................... 310/12.24; 310/12.33

(58) Field of Classification Search
USPC .............. 310/12.24, 14, 15, 17, 12.25, 12.26, 310/12.15, 12.02, 12.33
See application file for complete search history.

(56) References Cited

U.S. PATENT DOCUMENTS

| | | | |
|---|---|---|---|
| 4,071,042 A | | 1/1978 | Lombard et al. |
| 4,127,835 A | * | 11/1978 | Knutson ........................ 335/266 |
| 4,490,815 A | * | 12/1984 | Umehara et al. ................ 369/43 |
| 5,166,652 A | * | 11/1992 | Koyama et al. ............... 335/234 |
| 5,434,549 A | * | 7/1995 | Hirabayashi et al. ......... 335/229 |
| 5,478,650 A | | 12/1995 | Davanloo et al. |
| 5,896,076 A | | 4/1999 | van Namen |
| 6,239,517 B1 | * | 5/2001 | Nakamura et al. ......... 310/12.28 |
| 6,326,706 B1 | * | 12/2001 | Zhang ......................... 310/12.31 |
| 7,365,768 B1 | | 4/2008 | Ono et al. |
| 7,429,808 B2 | * | 9/2008 | Lehr et al. ................... 310/12.04 |
| 7,768,160 B1 | * | 8/2010 | Sahyoun .......................... 310/14 |
| 7,859,144 B1 | * | 12/2010 | Sahyoun .......................... 310/15 |
| 2006/0208600 A1 | | 9/2006 | Sahyoun |

FOREIGN PATENT DOCUMENTS

| | | |
|---|---|---|
| DE | 2621272 A1 | 11/1976 |
| DE | 3626254 A1 | 2/1988 |
| DE | 3717872 A1 | 12/1988 |
| DE | 19618355 A1 | 11/1997 |
| DE | 10323629 A1 | 10/2004 |
| DE | 102006006877 A1 | 8/2007 |
| DE | 102007051162 A1 | 5/2008 |
| DE | 102008038926 A1 | 2/2009 |
| EP | 0580117 A2 | 1/1994 |
| JP | 54121207 U | 8/1979 |
| JP | 11155274 A | 6/1999 |
| WO | 9918649 A1 | 4/1999 |
| WO | 2007067704 A2 | 6/2007 |

* cited by examiner

*Primary Examiner* — Dang Le

(74) *Attorney, Agent, or Firm* — St. Onge Steward Johnston & Reens LLC

(57) ABSTRACT

A linear motor for optical systems, for example, endoscopes, is described. The motor has a stator with a magnetic guiding member and two adjacently disposed coils which are energized in opposite directions. Furthermore permanent magnets polarized in opposite directions and in the axial direction are provided on both sides of the pair of coils. The armature of the motor has a permanent magnet which is polarized in the opposite direction to the permanent magnet of the stator and is connected to a pole piece at each end. The pole pieces are arranged so that in the rest position each pole piece lies at the centre of one of the coils. By applying current to the coil, the armature can be displaced from a rest position in the longitudinal direction.

14 Claims, 7 Drawing Sheets

LINEAR MOTOR WITH PERMANENT-MAGNETIC SELF-HOLDING

CROSS-REFERENCE TO RELATED APPLICATIONS

The present application claims priority German patent application No. 10 2010 000 582.7 filed on Feb. 26, 2010.

FIELD OF THE INVENTION

The invention relates to a linear motor in particular for optical systems. Such optical systems are used, for example, in endoscopes. In modern video endoscopes a camera chip and an appurtenant lens system are integrated in the endoscope tip. A miniaturized motor is required to adjust the focal length or the focus of the lens system.

BACKGROUND OF THE INVENTION

Classical endoscopes such as can be used, for example, for minimally invasive surgery, guide the image by means of rod lenses from the intracorporeal objective to the extracorporeal eyepiece. As a result of the rod lenses, the system is rigid and limited in optical quality. Modern video endoscopes use a camera chip in the endoscope tip. Such an endoscope is disclosed in U.S. Pat. No. 7,365,768 B1. This has a rigidly disposed lens in front of the camera chip. An adjustment of the focal length of the lens is not possible.

DE 196 18 355 C2 discloses a linear drive which can be integrated in endoscopes for adjusting the focal width of a lens system. For this purpose a permanent magnet is moved as an armature inside a stator coil. However, as a result of the large mass of the permanent magnet, the linear drive is sluggish. The relationship between the coil current and the armature position is not single-valued and necessitates an additional displacement sensor with positional regulation.

DE 37 17 872 C2 discloses a drive having an armature and a stator for a lens system in video cameras. The armature consists of two iron sleeves which are interconnected by a support for receiving the lens system. The stator has two coils and a single annular permanent magnet for generating the magnetic fields required for the movement between the coils. The complex structure of the drive can be readily implemented in video cameras having lens diameters in the centimeter range but is not scalable to the size required for endoscope applications in the millimeter range.

DE 103 23 629 A1 discloses a moving field linear motor which comprises at least three stator coils. A phase-shifted current supply to the coils produces a moving field which effects a displacement of the armature with axial permanent magnets. An expensive controlling circuit is required to produce the moving field.

Known from DE 10 2008 038 926 A1 is a linear drive including two axially polarized permanent magnets in the armature. The armature is deflected by the current supply to the stator coils in the axial direction. In addition, the stable positions of the armature are achieved by the pole piece mounted in the stator so that a continuous displacement of the armature in a cladding tube is rendered possible. A disadvantage here is the dependence of the stroke and the adjusting forces on the soft-magnetic stator pole pieces, with the result that a high precision is required in the manufacture and assembly of these parts.

SUMMARY OF THE INVENTION

It is the object of the invention to provide a linear motor having such small dimensions that this can be inserted in endoscopes. Furthermore, the linear motor should have a defined zero point position and a reproducible deflection as a function of the control signal. In addition, the linear motor should exhibit large driving forces with small mass and thereby render possible a rapid, continuous and exact positioning of the optical system in the largest possible range. At the same time, the beam path through the optical system must not be blocked during displacement of the components. The power loss of the linear motor should be low so that little heat is produced in the tip of an endoscope. The drive should be composed of as few as possible and as geometrically simple as possible individual components for simple manufacture and assembly.

In an embodiment the linear motor includes a stator and an armature which is linearly displaceable thereto. The stator has at least one coil and a magnetic guiding member on the outer side which is disposed at least largely parallel to the direction of movement. Furthermore, at least one axially magnetized permanent magnet is provided on the stator. The at least one coil is disposed in a plane with the at least one permanent magnet. The term of the plane in the case of a cylindrical arrangement relates to a cylindrical surface. The armature is enclosed by the at least one coil at least partially radially and has at least one permanent magnet and at least one pole piece. The magnetic flux of the at least one permanent magnet passes via the pole piece through the at least one coil. Advantageously, the field of the permanent magnet in the stator is parallel to the field of the permanent magnet in the armature, wherein the two fields penetrate through each other. In the resting position, i.e. without energizing, of the linear motor, each pole piece is located inside a coil, preferably at the coil centre. The armature itself has a gap or a hole in the axial direction, wherein, for example, an optical element can be accommodated.

In a particularly advantageous embodiment, the stator comprises a first coil and a second coil disposed adjacently thereto. Both coils have current flowing therethrough in the opposite direction, i.e. are energized. Furthermore, outside the two coils a first permanent magnet is disposed adjacent to the first coil and a second permanent magnet adjacent to the second coil. The two permanent magnets are magnetized axially and in the same direction. The armature has a first permanent magnet which is magnetized in the opposite direction to the permanent magnet of the stator. Furthermore, the first permanent magnet of the armature is connected on both sides to respectively one pole piece.

A further advantageous embodiment of this configuration comprises an additional first pole piece in the stator. This is preferably disposed centrally between the two coils.

In a further advantageous embodiment, the stator has a first coil and a second coil disposed adjacently thereto. Both coils have current flowing therethrough in opposite directions. A permanent magnet is disposed between the first coil and the second coil. The armature has a first permanent magnet which is magnetized in the opposite direction to the permanent magnet of the stator. Furthermore, the first permanent magnet of the armature is connected on both sides to respectively one pole piece.

In a further advantageous embodiment of this configuration, the stator additionally has a first pole piece adjacent to the first coil and a second pole piece adjacent to the second coil.

A further advantageous embodiment relates to a linear motor having a stator with a coil and oppositely magnetized permanent magnets disposed on both sides of the coil. The armature has two opposite magnetized permanent magnets between which a pole piece is disposed. The magnetization of the permanent magnets of armature and stator is also aligned in the opposite direction so that in each case north poles or south poles lie opposite one another between armature and stator.

A further embodiment relates to a linear motor having a stator with three coils, wherein the coils each have current flowing therethrough alternately in opposite directions. A permanent magnet is disposed on this side of this coil arrangement, wherein the two permanent magnets are oppositely magnetized. The armature has two permanent magnets which are also oppositely magnetized. The magnetization of the permanent magnets of armature and stator is also aligned in the opposite direction so that in each case, north poles or south poles lie opposite one another between armature and stator. Furthermore, a pole piece is attached between the permanent magnets and likewise respectively one pole piece is attached on both free sides of the permanent magnets.

A linear motor according to another embodiment preferably has a rotationally symmetrical armature and/or a rotationally symmetrical stator. The linear motor is preferably designed rotationally symmetrically with annular magnetic guiding member, pole pieces, permanent magnets and an annular coil. The armature and in particular the permanent magnets as well as the pole piece are preferably hollow-cylindrical, i.e. they have the form of a cylindrical sleeve. The beam path of an optical system can then run through the sleeve. In particular, a lens or another optical element can sit in the sleeve. Consequently, the focal length and/or the focus of the optical system can be adjusted by a displacement of the sleeve.

The pole piece and the magnetic guiding member must always include ferromagnetic and/or soft magnetic materials.

The linear motor can easily be miniaturized as far as a size of a few millimeters external diameter. In a motor having an external diameter of a few millimeters, the travel distance between the two end positions of the armature is typically about 1 to 3 mm.

In a further embodiment, there is a sliding layer between the stator and the armature. This can be implemented as a sliding sleeve in particular in the case of a rotationally symmetrical arrangement. In order to influence the magnetic fields as little as possible, the sliding layer should consist of a non-magnetic-field-conducting material, in particular of a non-ferromagnetic material.

A linear motor according to another embodiment can also consist of solid material and have a plunger at one end for the nanopositioning of instruments. Such a device can preferably be used in molecular biology, microelectronics or neurosurgery.

It is particularly favorable if the coil is supplied with a direct current with a superposed alternating current of small amplitude and having a frequency up to a maximum of 1 kHz. The static and sliding friction can be reduced by this means.

A further embodiment is a method for operating a linear motor, wherein the linear motor is supplied with a direct current and a superposed alternating current of small amplitude and having a frequency up to a maximum of 1 kHz. The static friction or sliding friction in the interior of the motor can be reduced by this means.

BRIEF DESCRIPTION OF THE DRAWINGS

In the following, the invention will be described by way of example, without limitation of the general inventive concept, on examples of embodiment and with reference to the drawings.

DETAILED DESCRIPTION OF THE INVENTION

Figure 1:
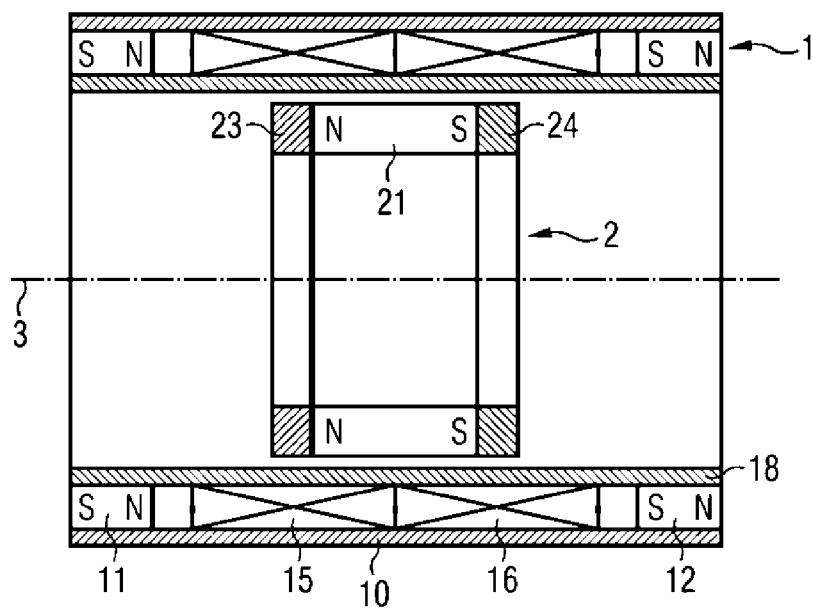
FIG. 1 shows schematically a linear motor.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

FIG. 1 shows schematically an exemplary embodiment of an arrangement in cylindrical design in sectional view. The stator 1 comprises a magnetic guiding member 10 in the form of a soft-magnetic tube, a first coil 15 and a second coil 16 being disposed in the bore whereof. Neighboring coils each have current flowing therethrough in opposite directions. A first permanent magnet 11 is disposed on one side of the coils. A second permanent magnet 12 is disposed on the other side of the coils. Both permanent magnets are axially magnetized in the same direction. A sliding layer 18 in the form of a sliding sleeve terminates the stator 9 here towards the inside and provides a low-friction surface for the armature. The sliding sleeve preferably consists of a non-ferromagnetic material. The armature 2 here comprises a permanent magnet 21 and a first pole piece 23 on the side of the north pole of the permanent magnet and a second pole piece 24 on the side of the south pole. The armature is aligned in such a manner that the north pole of the magnet 21 is opposite the north pole of the permanent magnet 11 in the stator. Accordingly, the south pole of the magnet 21 is then opposite the south pole of the permanent magnet 12. As a result, a repulsive reluctance force is obtained in both directions on the armature and consequently a stable central point position in the centre between the two permanent magnets 11, 12 of the stator. An element to be positioned, such as an optical component, can be inserted into the bore of the armature. The armature is axially displaceable in both directions inside the sliding sleeve. The central axis 3 is also the axis of rotation in arrangements having a rotationally symmetrical structure. The surface of the sliding layer preferably comprises a material having a low coefficient of friction, for example, PTFE (polytetrafluorethylene), silicon nitride, silicon carbide, poly-para-xylene polymers or DLC (diamond like carbon) such as is disclosed, for example, in U.S. Pat. No. 5,478,650. It can compensate for unevennesses on the side of the stator facing the armature.

The particular feature of this drive lies in the incorporation of permanent magnets not only in the armature but additionally also in the stator. High magnetic flux densities can be produced hereby and in particular, the arrangement thereof is used to adjust a stable axial central position of the armature (comparable to a centering mechanical spring, but without any friction). As a result of energizing the coils, the armature is deflected against an increasing axial restoring force through the magnet arrangement in stator and armature. A current-proportional deflection of the armature is hereby rendered possible.

Figure 2:
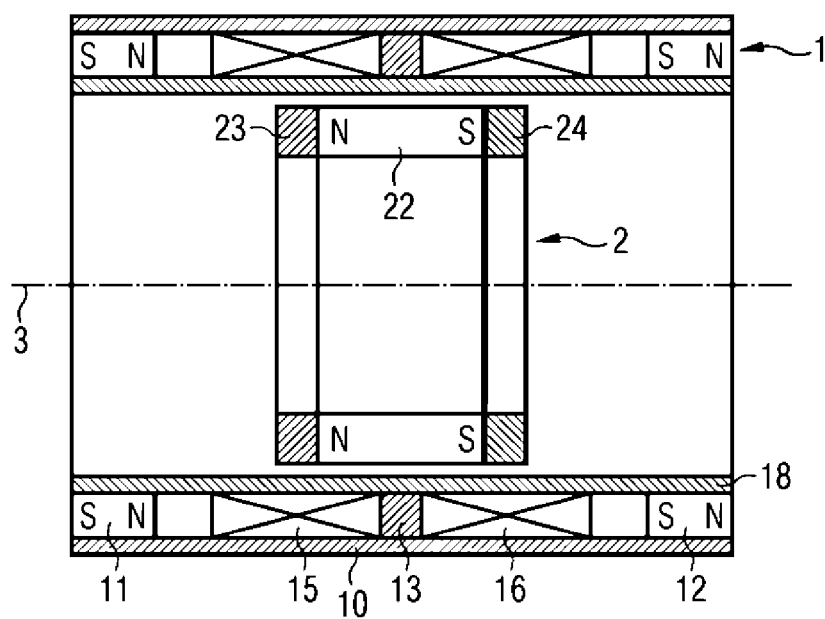
FIG. 2 shows a variant of the linear motor with an additional pole piece in the stator.

FIG. 2 shows as an example a further embodiment. A first pole piece 13 is disposed in the stator between the first coil 15 and the second coil 16.

Figure 3:
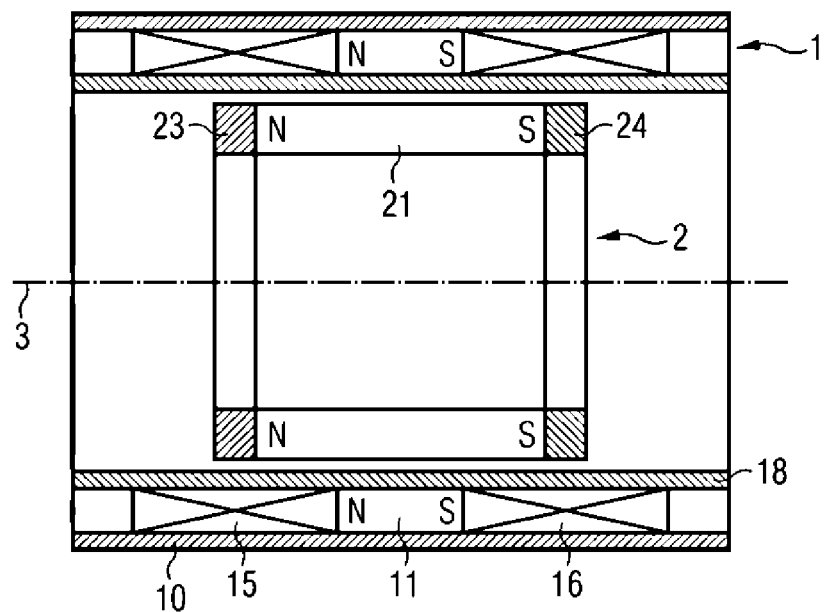
FIG. 3 shows a further variant of the linear motor with a permanent magnet between the coils.

FIG. 3 shows a further embodiment. Here only one single permanent magnet 11 is provided on the stator. This is disposed between the first coil 15 and the second coil 16.

Figure 4:
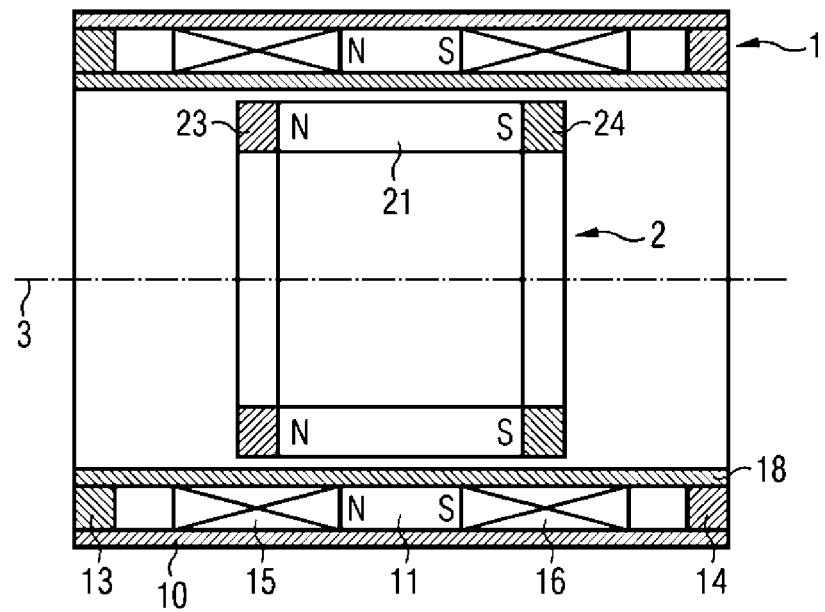
FIG. 4 shows a variant of the linear motor from FIG. 3, wherein additional pole pieces are provided on the stator.

FIG. 4 shows a further variant of the linear motor according to FIG. 3. In this case, additional pole pieces 13, 14 are provided at the side outside the coils 15 and 16.

Figure 5:
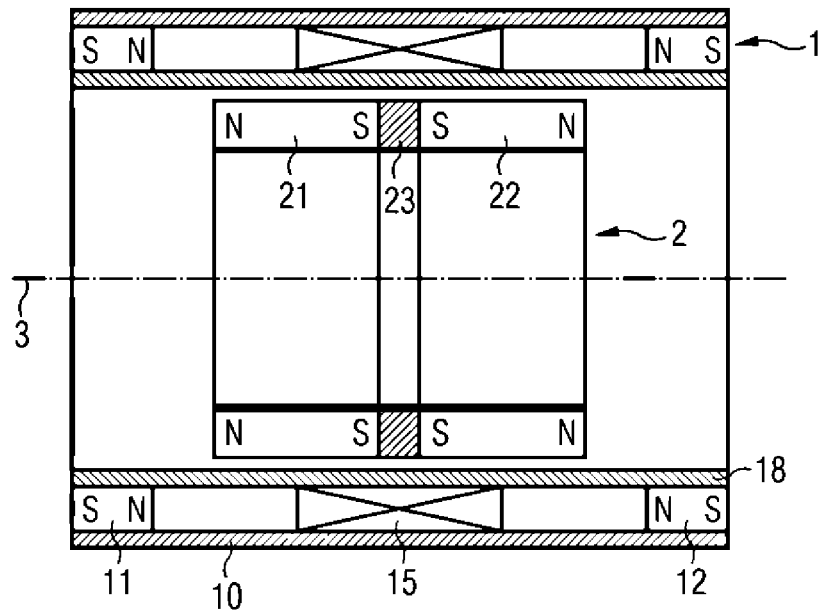
FIG. 5 shows a further variant of the linear motor with only one coil.

FIG. 5 shows a further variant of the linear motor with only one coil. Here the stator has only one coil 15 with two permanent magnets 11, 12 arranged at the side of the coil. The two permanent magnets 11, 12 are oppositely magnetized in the axial direction. At the centre the armature has a first pole piece 23 on which respectively a first permanent magnet 21 and a second permanent magnet 22 are arranged laterally. The two permanent magnet are also axially oppositely magnetized. In this example, the two south poles of the permanent magnets 21 and 22 lie on the first pole piece 23. The permanent magnets 11, 12 of the stator are axially oppositely magnetized to the corresponding magnets of the armature.

Figure 6:
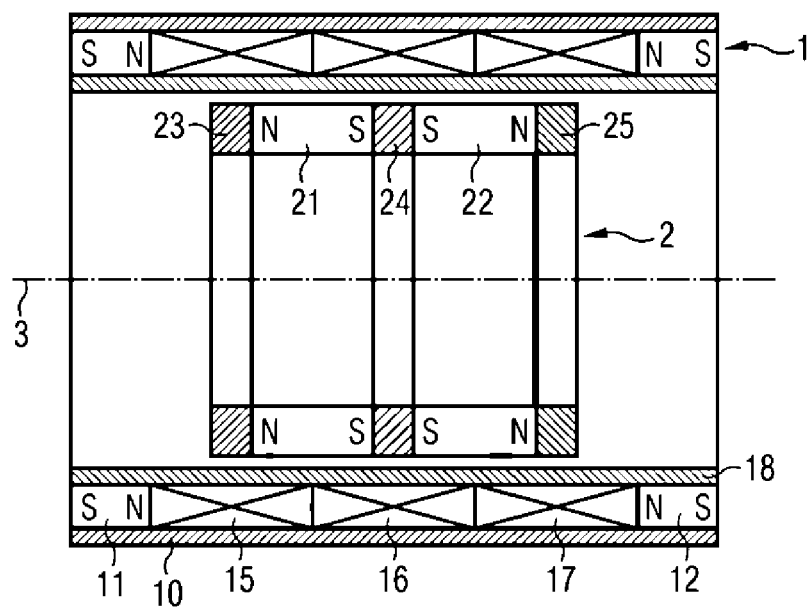
FIG. 6 shows a further embodiment with three coils.

A further embodiment with three coils is disclosed in FIG. 6. Here the stator has a first coil 15, a second coil 16 and a third coil 17 located adjacently to one another. If the second coil 16 has current flowing therethrough in a first direction, the two coils 15, 17 disposed to the side of said coil have current flowing therethrough in the opposite direction. Laterally adjacent to the coils a first permanent magnet 11 and a second permanent magnet 12 are arranged in an axially oppositely magnetized manner. The armature has three pole pieces 23, 24 and 25. Each pole piece is within a coil. A first permanent magnet 21 is disposed between the first pole piece 23 and the second pole piece 24. A second permanent magnet 22 is located between the second pole piece 24 and the third pole piece 25. The magnetization of the permanent magnets is as in the arrangement according to FIG. 5. As a result of the higher number of coils, the adjusting forces can be increased here and the positioning accuracy can be increased.

The different embodiments shown herein are preferably designed mirror-symmetrically to a plane which stands vertically on the central axis. This does not relate to the directions of magnetization of the permanent magnets. These are aligned according to their function. As a result of the mirror-symmetrical arrangement, a symmetrical current-distance characteristic and a stable zero point position of the armature in the centre of the arrangement are obtained.

The length of the magnetic guiding member 10 is longer than the length of the armature 2. It is particularly advantageous if the length of the magnetic guiding member is greater than the length of the armature 2 plus the maximum traveling distance of the armature.

The linear motor enables an exact adjustment of the position of the armature relative to the stator between two end positions. In the linear motor a unique position of the armature in relation to the stator corresponds to each coil current. Consequently, the armature can be continuously displaced in the travel range by means of an adjustment of the coil current. As a result of this unique assignment between the coil current and the armature position, the path measurements necessary according to the prior art to determine the position of the armature can be dispensed with. The individual components have a simple geometry (rings, sleeves) and therefore can easily be manufactured and assembled.

The pole piece and the magnetic guiding member must always include ferromagnetic and/or soft magnetic materials.

The coil can be wound onto a coil bobbin or without a coil bobbin as desired. It can also be multi-part, i.e. it can consist of a plurality of windings.

Alternatively the linear motor can be implemented with a flat stator, e.g. having a plate-shaped structure and a likewise flat or plate-shaped pole piece of the armature. Alternatively, a plurality of linear motors disposed around a cylinder or a polygonal body can also be provided. A stable guidance is obtained, for example, in the case of a uniform arrangement of linear motors around a cylinder.

Figure 12:
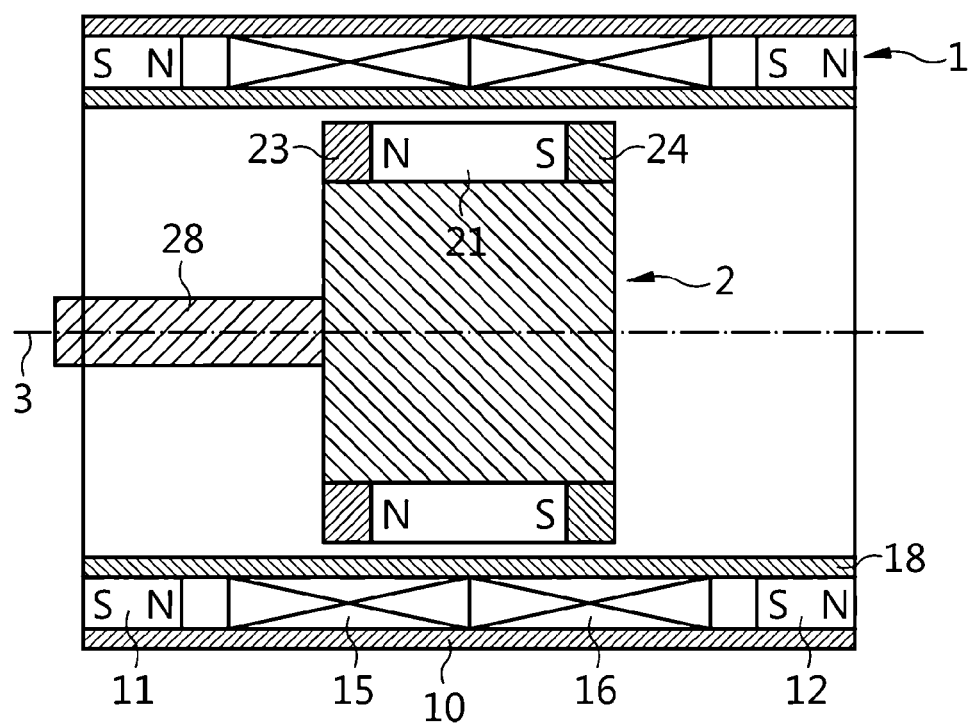
FIG. 12 shows the linear motor from FIG. 1 wherein the armature consists of solid material and has a plunger.

FIG. 12 shows a linear motor according to another embodiment. The armature consists of solid material 27 and has a plunger 28 at one end for the nanopositioning of instruments. Such a device can preferably be used in molecular biology, microelectronics or neurosurgery.

It is particularly favorable if the coil is supplied with a direct current with a superposed alternating current of small amplitude and having a frequency up to a maximum of 1 kHz. The static and sliding friction can be reduced by this means.

Figure 7:
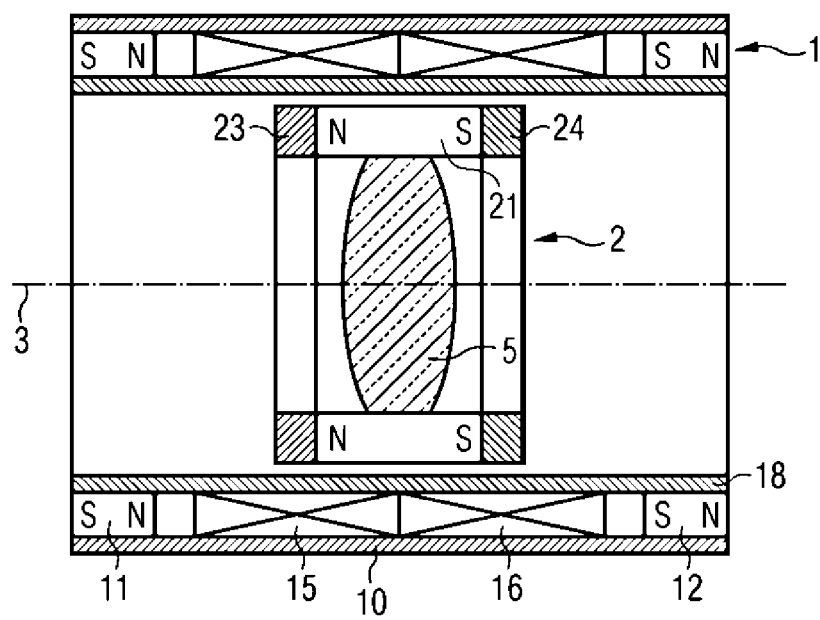
FIG. 7 shows the linear motor from FIG. 1 with a lens.

FIG. 7 shows a linear motor from FIG. 1, wherein another lens 5 is shown which can be displaced by the linear motor in the direction of the central axis 15.

Figure 8:
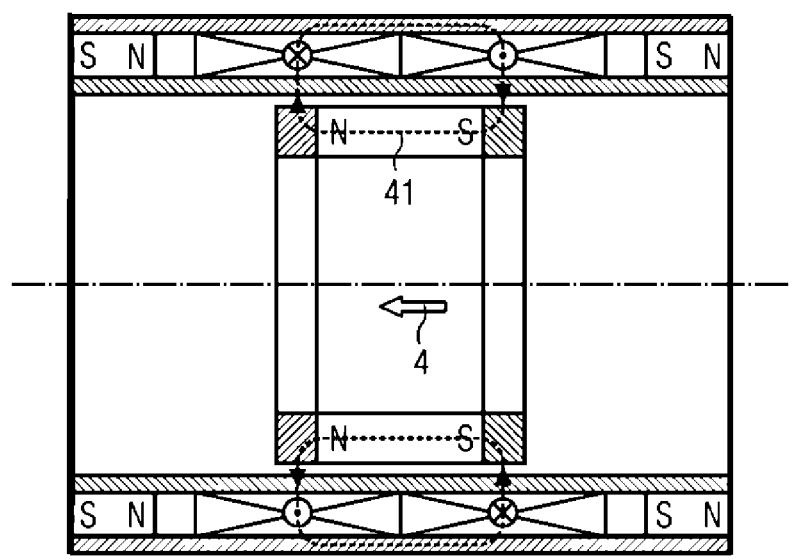
FIG. 8 shows the field behavior in the linear motor with energized coil.

FIG. 8 shows a diagram with the magnetic circuits with energized coils. Here, as indicated by the direction arrows, a current is passed through the coils so that in the coil 15 in the upper half of the figure the current flows into the plane of the drawing and accordingly in the lower half of the figure, it flows out from the plane of the drawing. The current flow through the coil 16 takes place in the reverse direction. The magnetic flux from the permanent magnets 21 passes via the two pole pieces 23 and 24 as well as the magnetic guiding member 10 through the coils 15 and 16. Due to the current flow through the coils, a Lorentz force is produced on the armature in the direction of movement 4. This counteracts the reluctance force between the permanent magnet 21 of the armature and the permanent magnets 11, 12 of the stator.

Figure 9:
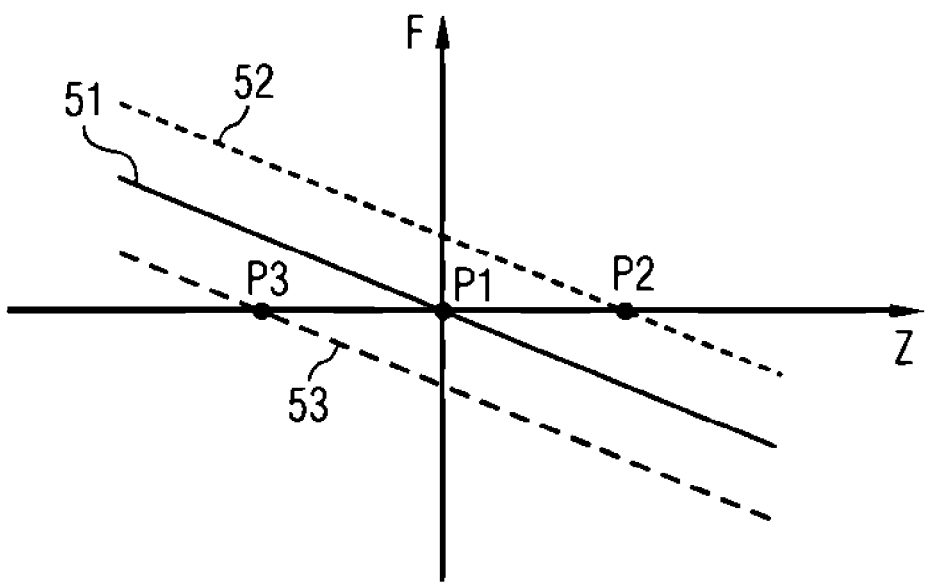
FIG. 9 shows force-distance characteristics of the linear motor for different coil currents.

FIG. 9 shows the force-distance characteristics for various coil currents. In the diagram, the force F on the armature is plotted as a function of the deflection z of the armature. A positive force F is plotted upwards and a positive deflection z is plotted to the right. The curve 51 shows the force-distance characteristic when the coil is non-energized, that is at a zero coil current. In the event of a positive deflection z of the armature, that is in the z-direction to the right, a negative restoring force F is obtained as a result of the reluctance forces, which attempts to hold the armature at its position. In the position P1 the restoring force is zero. Consequently, at this point the armature will adopt a stable position without energizing the coil. If, as a result of externally acting forces, for example, acceleration forces, the armature is pushed from this stable position in one of its directions of movement, repelling forces act, which push the armature back into the central position. The magnetic forces hold the armature in this position comparably to a mechanical spring. With a coil current in a first direction, an additional Lorentz force is superposed on the reluctance forces. The curve 51 is thus shifted in the direction of the curve 52. This results in the restoring force zero at the point P2 which lies remote from the point P1 in the positive z-direction so that the armature adopts a new stable position at this point. The same occurs with a current of opposite polarity but in the reverse direction. The curve 51 is shifted in the direction of the curve 53. The point P3 with the zero restoring force now lies in the opposite direction of the original point P1.

The term coil current is used here. This is independent of the number of coils provided in the respective embodiment. Naturally, adjacent coils have current flowing therethrough in opposite directions. When the polarity is reversed, the polarity of the currents through all the coils is therefore reversed. The concept of the current intensity relates to the current through a coil.

Figure 10:
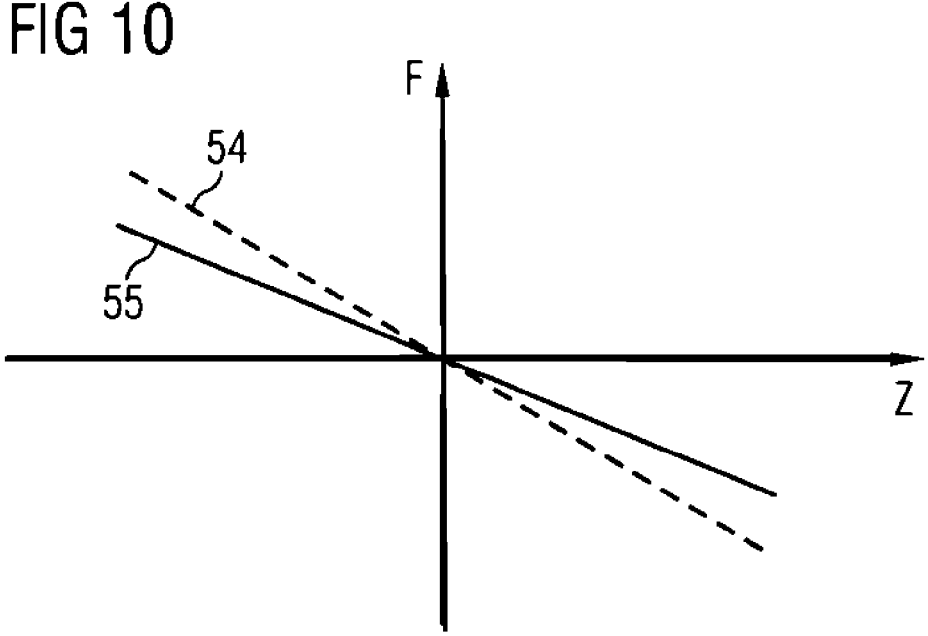
FIG. 10 shows force-distance characteristics of the linear motor with and without pole piece in the stator

FIG. 10 shows the effect of a pole piece 13, 14 in the stator by reference to force-distance characteristics. The characteristics relate to the non-energized coils. The diagram fundamentally shows as in the previous figure, the function of the restoring force F on the armature as a function of the deflection z. The curve 54 is formed in a typical arrangement. If an additional pole piece 13, 14 is now integrated in the stator, a reduction of the restoring reluctance forces and therefore a flatter characteristic is obtained. Consequently, the characteristic can be adjusted in wide ranges by incorporating additional pole pieces and naturally also by means of the dimensioning thereof. An advantage of a flatter characteristic is, for example, that a lower coil current is required to actuate the armature, which in turn leads to a lower power loss in the coils. Specifically in endoscope instruments it is desirable to keep the power loss in the tip of the instrument as low as possible in order to influence the site of the examination as little as possible. Here the use of an additional pole piece provides a simple optimizing mechanism.

Figure 11:
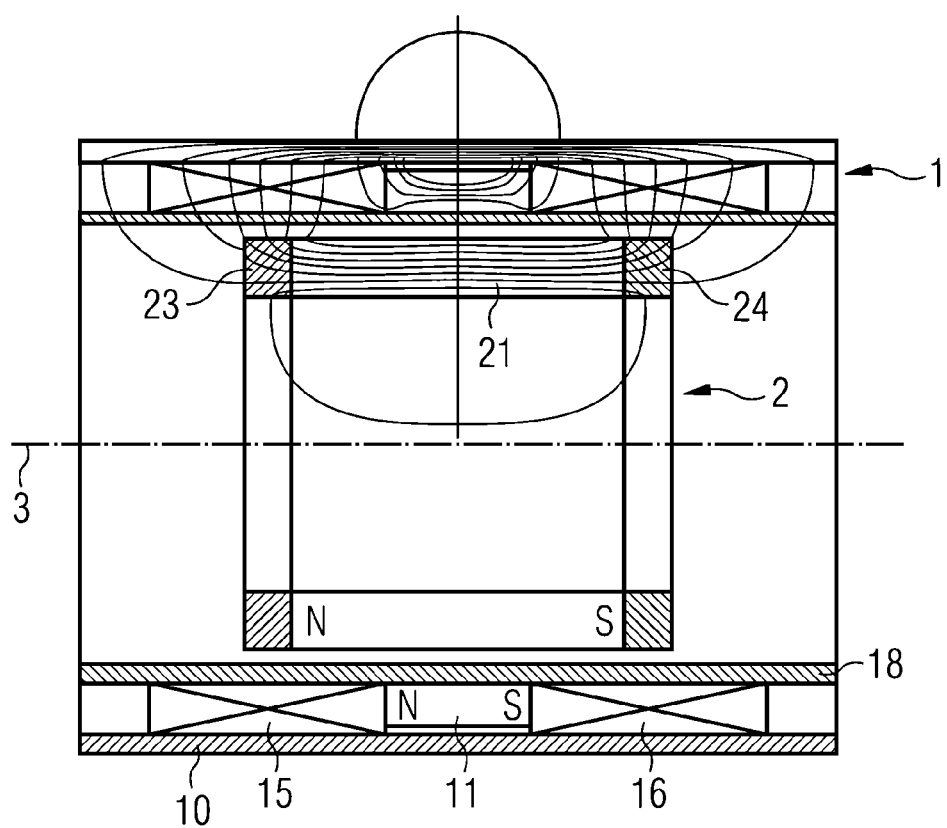
FIG. 11 shows the field distribution of a linear motor from FIG. 3 in the non-energized state.

FIG. 11 shows the field distribution of a linear motor from FIG. 3 in the non-energized state. The magnetic field lines in the upper half of a sectional view from FIG. 3 are depicted here. In fact, the field, like the entire arrangement, is rotationally symmetrical.

It will be appreciated to those skilled in the art having the benefit of this disclosure that this invention is believed to provide linear motors. Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A linear motor including
    a stator having at least one coil and at least one axially magnetized permanent magnet, which are enclosed by a magnetic member comprising magnetic material, the at least one coil being disposed in a plane with the at least one permanent magnet; and
    an armature which is surrounded radially by the at least one coil and which is displaceable parallel to the stator, having a gap or a bore in the axial direction and having at least one axially magnetized permanent magnet and a number of pole pieces corresponding to the number of coils;
    wherein the magnetic working flux of the at least one permanent magnet passes via the pole pieces through the at least one coil; and
    without the linear motor being energized, each pole piece is located inside a coil.

2. The linear motor according to claim 1, wherein the stator comprises a first coil and an adjacently disposed second coil;
    the first coil being energized in the opposite direction to the second coil;
    a first permanent magnet is provided adjacent to the first coil;
    a second permanent magnet is provided adjacent to the second coil;
    wherein the two permanent magnets are magnetized in the same direction; and
    the armature has a first permanent magnet which is magnetized in the opposite direction to the permanent magnets of the stator and is connected at each end to a pole piece.

3. The linear motor according to claim 2, wherein the stator has a first pole piece which is disposed between the first coil and the second coil.

4. The linear motor according to claim 1, wherein the stator comprises a first coil and an adjacently disposed second coil;
    the first coil is energized in the opposite direction to the second coil;
    a first permanent magnet is provided between the first coil and adjacent to the second coil; and
    the armature has a first permanent magnet which is magnetized in the same direction as the first permanent magnet of the stator and is connected at each end to a pole piece.

5. The linear motor according to claim 4, wherein the stator has a first pole piece adjacent to the first coil and a second pole piece adjacent to the second coil.

6. The linear motor according to claim 1, wherein the stator comprises a first coil;
    a first permanent magnet being provided adjacent to the first coil; and
    a second permanent magnet being provided adjacent to the second coil;
    the two permanent magnets being magnetized in opposite directions;
    the armature has a first permanent magnet on the side of the first permanent magnet of the stator which is magnetized in the opposite direction to the first permanent magnet of the stator;
    the armature further has a second permanent magnet on the side of the second permanent magnet of the stator which is magnetized in the opposite direction to the second permanent magnet of the stator; and
    a first pole piece is disposed between the first permanent magnet of the armature and the second permanent magnet of the armature.

7. The linear motor according to claim 1, wherein the stator comprises a first coil, an adjacently disposed second coil and a further adjacently disposed third coil;
    the first coil is energized in the same direction as the third coil while the second coil is energized in the opposite direction to the first coil and the third coil ;
    a first permanent magnet is provided adjacent to the first coil;
    a second permanent magnet is provided adjacent to the third coil;

the two permanent magnets are magnetized in opposite directions;

the armature has a first permanent magnet on the side of the first permanent magnet of the stator which is magnetized in the opposite direction to the first permanent magnet of the stator;

the armature further has a second permanent magnet on the side of the second permanent magnet of the stator which is magnetized in the opposite direction to the second permanent magnet of the stator;

a first pole piece is disposed on one side of the first permanent magnet;

a second pole piece is disposed between the first permanent magnet of the armature and the second permanent magnet of the armature; and a third pole piece is disposed on a side of the second permanent magnet.

8. The linear motor according to claim 1, wherein the length of the armature is smaller than the length of the magnetic member.

9. The linear motor according to claim 1, wherein an optical element can be accommodated in the interior of the armature.

10. The linear motor according to claim 1, wherein the armature is rotationally symmetrical.

11. The linear motor according to claim 1, wherein the stator is rotationally symmetrical.

12. The linear motor according to claim 1, wherein a sliding sleeve including a material having a low coefficient of friction on the surface is disposed between stator and armature.

13. The linear motor according to claim 1, wherein the armature consists of solid material and merely has a plunger for the nanopositioning of instruments.

14. A method for operating a linear motor according to claim 1, wherein a very small alternating current having frequencies up to a maximum of 1 kHz is superposed on the direct current through the coil to reduce the static and sliding friction.

* * * * *